United States Patent [19]

Robinson et al.

[11] Patent Number: 4,559,450
[45] Date of Patent: Dec. 17, 1985

[54] QUANTITATIVE COMPOSITIONAL ANALYSER FOR USE WITH SCANNING ELECTRON MICROSCOPES

[75] Inventors: Vivian N. E. Robinson, Oyster Bay; Nicholas G. Cutmore, Randwick, both of Australia

[73] Assignee: Unisearch Limited, Kensington, Australia

[21] Appl. No.: 519,056

[22] Filed: Aug. 1, 1983

[30] Foreign Application Priority Data

Aug. 6, 1982 [AU] Australia .................. PF5247

[51] Int. Cl.⁴ ............................. G01N 23/225
[52] U.S. Cl. ............................ 250/310; 250/307
[58] Field of Search ............... 250/306, 307, 310, 305, 250/311, 309

[56] References Cited

U.S. PATENT DOCUMENTS 3,103,584  9/1963  Shapiro et al. ............ 250/307
4,034,220  7/1977  le Gressus et al. .......... 250/310

FOREIGN PATENT DOCUMENTS 405474   3/1965  Japan ..................... 250/310
1014875 12/1965  United Kingdom .

OTHER PUBLICATIONS

J. W. Colby; Backscattered and Secondary Electron Emission as Ancillary Techniques in Electron Probe Analysis, Adv. Electron. Electron Phys., Supp. 6, pp. 177–196 (1969).
R. Castring; Electron Probe Analysis, Adv. Electron. Electron Phys., 13, (1960), pp. 317–386.
"Backscattered Electrons as an Analytical Technique," R. E. Ogilve, Fourth Symposium on Electron Beam Tech., Mar. 1962.

Primary Examiner—Bruce C. Anderson
Assistant Examiner—Paul A. Guss
Attorney, Agent, or Firm—c/o Ladas & Parry

[57] ABSTRACT

An analysis system for a scanning electron microscope having a backscattered electron detector. The output of the detector is amplified, processed by an analogue to digital converter, multi-channel analyser, and digital conversion and processing circuit to generate a signal indicative of the atomic number factor of the specimen. Calculation of stoichiometric valence combinations of non-elemental specimens is also disclosed. A calibration device is also disclosed.

10 Claims, 9 Drawing Figures

QUANTITATIVE COMPOSITIONAL ANALYSER FOR USE WITH SCANNING ELECTRON MICROSCOPES

The present invention relates to scanning electron microscopes (SEM) and, in particular, to the use of equipment which enables such microscopes to carry out quantitative compositional analysis.

Hitherto, analysis of samples of either elements or compounds has been carried out by energy dispersive X-ray spectroscopy (EDS) or wavelength dispersive X-ray spectroscopy (WDS). However both of these procedures suffer from many disadvantages such as relatively high cost, the time taken for analysis, the relatively limited range of applicability, and so on.

The present invention is based upon the experimentally verified relationship that for a scanning electron microscope the shape of curve of the backscattered electron (BE) detector signal output versus atomic number (Z) is substantially independent of the detector, the beam voltage and the working distance employed in almost all usual working situations.

The unique shape of this curve means that the backscattered electron detector signal output can be calibrated at any microscope operating condition, accelerating voltage, beam current, working distance, within the constraints to be outlined hereafter. One calibrated, the output of the detector can be used as a direct measure of the atomic number factor (ANF) of the sample being examined. The atomic number factor so determined has the following important properties:

(i) The atomic number factor for an element is the same as the atomic number of the element.

(ii) The atomic number factor for a compound is a functionally calculable combination of all of the elements in the compound, including all light elements undetectable by EDS and WDS.

This present invention relates to a system which uses the signal output of a backscattered electron detector to measure the atomic number factor of a sample, the then uses this atomic number factor to calculate a chemical formula or composition for sample.

According to one aspect of the present invention there is disclosed an analysis system adapted for connection to a scanning electron microscope or equivalent device for generating and controlling an electron beam, said system comprising a backscattered electron detector, an amplifier connected to the output of said detector, an analogue to digital converter connected between said amplifier and a multi-channel analyser, a digital conversion and processing circuit connected to said multi-channel analyser to convert the digitised backscattered electron signal produced by said analogue to digital converter into a normalised backscattered electron signal indicative of the atomic number factor of the specimen, or a region thereof, associated with said detector, and means to display and/or record said normalised backscattered electron signal.

According to another aspect of the present invention, there is disclosed a technique for using the atomic number factor generated above to calculate a possible chemical formula or formulation for the specimen being studied, such calculation needing only the input of the elements detected by an energy dispersive x-ray detector system and the relative heights or ratios of the said peaks, with the calculation being based upon the stoichiometric considerations of the limited valence combinations of the elements in the material.

According to another aspect of the present invention there is disclosed a calibration apparatus for a backscattered electron detector, said calibration apparatus comprising an electron scattering or deflecting member externally movable relative to said detector so as to be placed in, or affect the path of, the electron beam of said detector to scatter or deflect part or all of said beam into at least a portion of the active detection region of said detector or to place a portion of the active region of said detector directly in the path of said electron beam thereby permitting the beam current and/or detector amplification setting to be monitored. Preferably the calibration apparatus takes the form of a metal plate resiliently biassed out of said electron eam but movable against the action of a spring, for example, to be momentarily inserted in the beam adjacent the detector. The preferred metal is copper.

Naturally, it is desirable that the above described analysis system is fitted with the above described calibration or beam monitoring device. Similarly it is desirable that the analysis system has an electron optical device which is fitted with a calibration or beam current monitoring device attached to the final aperture, the output of the current monitoring device being amplified and fed into either the amplifier for the purpose of adjusting detector gain to compenste for beam current drift, or the digital conversion circuit for the purpose of recalibrating the display means, should such recalibration be necessary because of beam current drift. For reasons of economy, normally such an electron optical device would be an alternative to the above described calibration device. However, both can be used together.

As a further improvement the system described preferably contains a logic unit which contains a facility for determining the normalised backscattered electron signal, and also calculating the atomic number factor of a compound containing two or more elements. Preferably the logic unit contains a facility for determining or taking into account the extent of voids and imperfections in the sample, thus determining microscopic variations in the density of a sample.

Furthermore, a digital to analogue converter is preferably fitted to the multi-channel analyser and/or the digital conversion circuit, together or separately, or in any combination, in which the signal from selectable channels in the multi-channel analyser is fed into the SEM display unit, either directly, through a control or mixing unit, or is superimposed upon the normal SEM signal, or in any combination thereof.

Methods of sample analysis and detector calibration are also disclosed.

Embodiments of the present invention will now be described with reference to the drawings in which.

Figure 1:
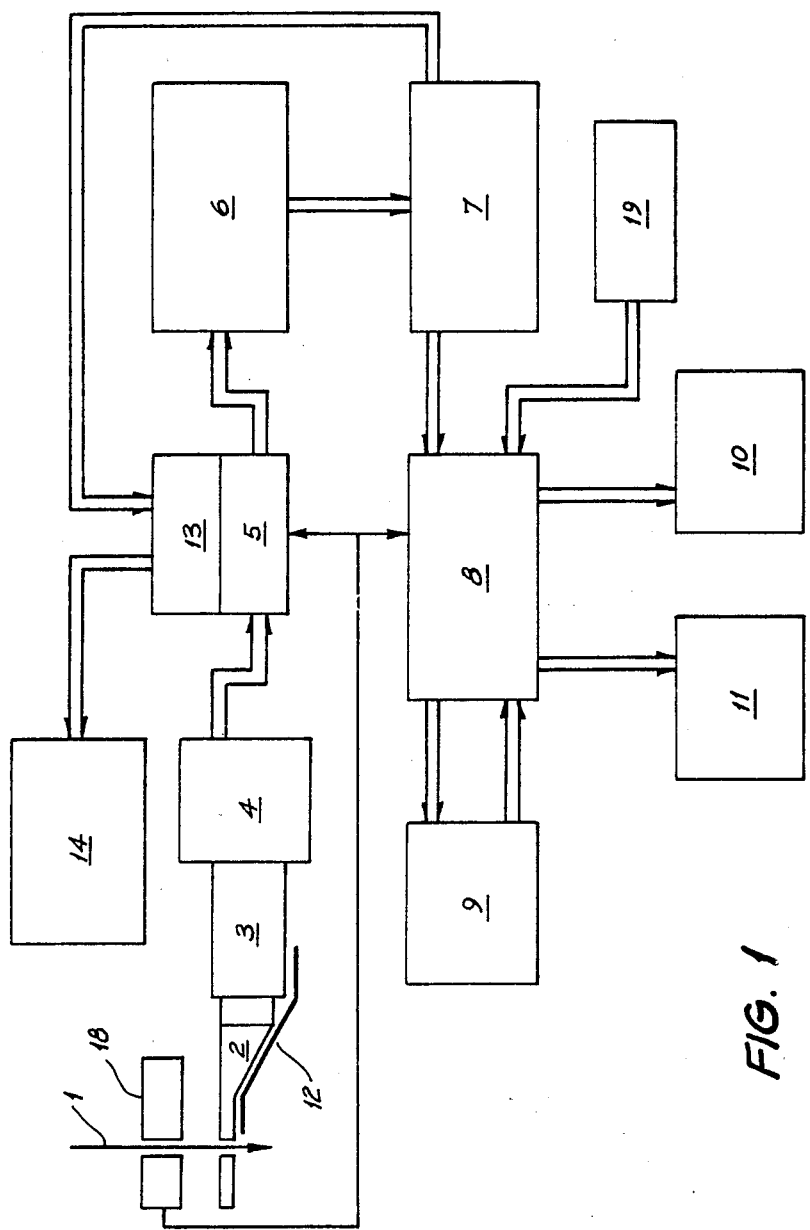
FIG. 1 is a block diagram of the analyser system of the preferred embodiment.

Turning now to FIG. 1, the preferred embodiment of an analysis system which can determine the chemical composition of some compounds on a microscopic scale, is illustrated in block schematic form. The system attached to a scanning electron microscope (SEM) or other electron optical equipment capable of generating an electron beam 1.

The system includes a backscattered electron detector 2, which can comprise a scintillation device, associated photomultiplier tube 3 and pre-amplifiers 4. Also included is a main amplifier 5 which can amplify the signal to a form acceptable to an analogue to digital converter 6. The analogue to digital covnerter 6 feeds into a multi-channel analyser 7, a digital conversion and processing circuit 8 which can read the multi-channel analyser display, and a logic circuit 9 which can both control the digital conversion and processing circuit 8 and feed information into it. Analyser 7, digital circuit 8 and logic circuit 9 can be incorporated into one unit.

Display and output units 10, 11 fed by the digital conversion and processing circuit 8 and logic circuit 9 can be used to visualise the results. The backscattered electron detector 2 preferably contains a calibration device 12 which consists of a shutter, rod or electron deflection device which can be placed under the beam 1 and deflect a portion, or all, of the electron beam 1 back into the detector 2. The pre-amplifier 4 and amplifier 5 can contain a control circuit 13 which can be used to provide independent control of signal intensity and amplitude for viewing on the scanning electron microscope viewing screen 14.

The control circuit 13 also contains a digital to analogue conversion circuit capable of taking the signal from selectable channels in the multi-channel analyser 7 and feeding it into the SEM display, either directly through a control unit or superimposed upon the normal signal through a missing unit, or in any combination thereof.

The logic cicuit 9 enables the conversion of the signal output of the backscattered electron detector 2 into the normalised backscattered electron signal of the sample which is used to calculate the atomic number factor of the sample. The logic circuit 9 also allows calculation of the normalised backscattered electron signal and/or the atomic number factor of a material of known chemical composition, plus the calculation of the ratio of elements present in a compound based upon knowledge of the normalised backscattered electron yield and/or atomic number factor of the specimens.

The analogue to digital converter 6, multi-channel analyser 7, digital conversion and processing circuit 8, logic circuit 9, display unit 10 and output unit 11 are of a type in common use in the industry. For example, the analogue to digital converter, 6, could be an AD5-74AKD manufactured by Analogue Devices Inc. The multi-channel analyser 7, and digital conversion and processing circuit 8 could be combined in a Z80A manufactured by Zylog Inc. The logic circuit 9 could be contained in a NM2732 manufactured by National Semiconductor Inc. The display unit 10 could be high resolution RGB colour video monitor manufactured by OKI Electric Company, Japan.

Preferably the beam current 1 is monitored by means of a conventional beam current monitor 18 attached to the final aperture of the electron microscope. The output of the current monitor 18 can be used as a feedback signal to control either the gain of the amplifier 5 and/or to provide an input for the digital conversion and processing circuit 8 which effectively re-calibrates the display and output units 10, 11 for any drift in beam current.

Should the specimen to be analysed not be an element, the specimen can be subject to energy dispersive X-ray spectroscopy in an energy dispersive X-ray detector system 19. A suitable X-ray detector system is that sold under the trade name PGT System 4 by Princeton-Gamma Tech. of Princeton, N.J., U.S.A. The output data of the system 19 including data on the relative intensity of detected elements is supplied to the digital conversion and processing circuit 8 for stoichiometric calculation of the valence combinations of the specimen in a manner to be described hereafter.

There are many different types of backscattered electron detectors available in the industrial field. Any type of backscattered electron detector can be used in this analyser system. These can include solid state detectors, either annular, quadrant, multiple array or other types; scintillator-photomultiplier types, either wide angle, multiple array, directional, high or low take off angle or other type; or other types such as a converter backscattered electron detector, channel plate, low loss detector or any other type of detector designed to detect backscattered electrons.

The only specific properties that the detector 2 must possess are (i) an ability to give off a signal when a backscattered electron impinges upon it and (ii) a frequency response or bandwidth greater than 100 Hz.

Associated with the detector 2 and interior of a vacuum port 20 (FIG. 2) is the calibration device 12. The calibration device 12 essentially consists of a plate 21 or a shutter, rod or other electron scattering device. Alternatively, an electron deflection device such as a magnetic field generator (not illustrated) can be used. The plate 21, scattering or deflection device has the property of being able to scatter or deflect part or all of an incident electron beam in a controlled manner into an active portion of the backscattered electron detector 2, thus generating a signal. One other property it must possess is an ability to be moved into and out of the path of the incident electrons. That is, it must be able to be moved, adjusted or activated either mechanically, electronically or by any other means. p In the preferred embodiment of the calibration device illustrated in FIGS. 2 and 3, the shutter or plate 21 is mounted on a rod 22 which passes through the vacuum port 20 and a guide 23. A helical spring 24 is located on the rod 22 between the guide 23 and a step 25.

Figure 2:
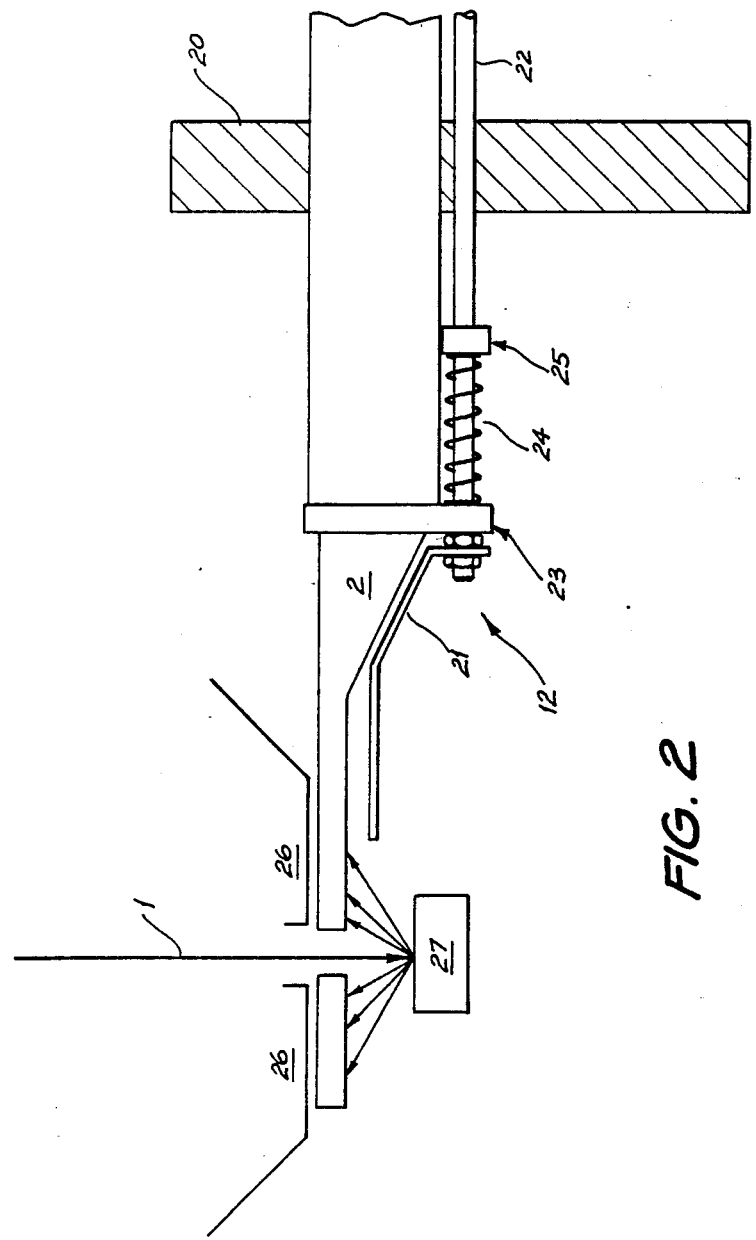
FIG. 2 is a longitudinal cross-sectional view through the backscattered electron detector showing the calibration device retracted.
Figure 3:
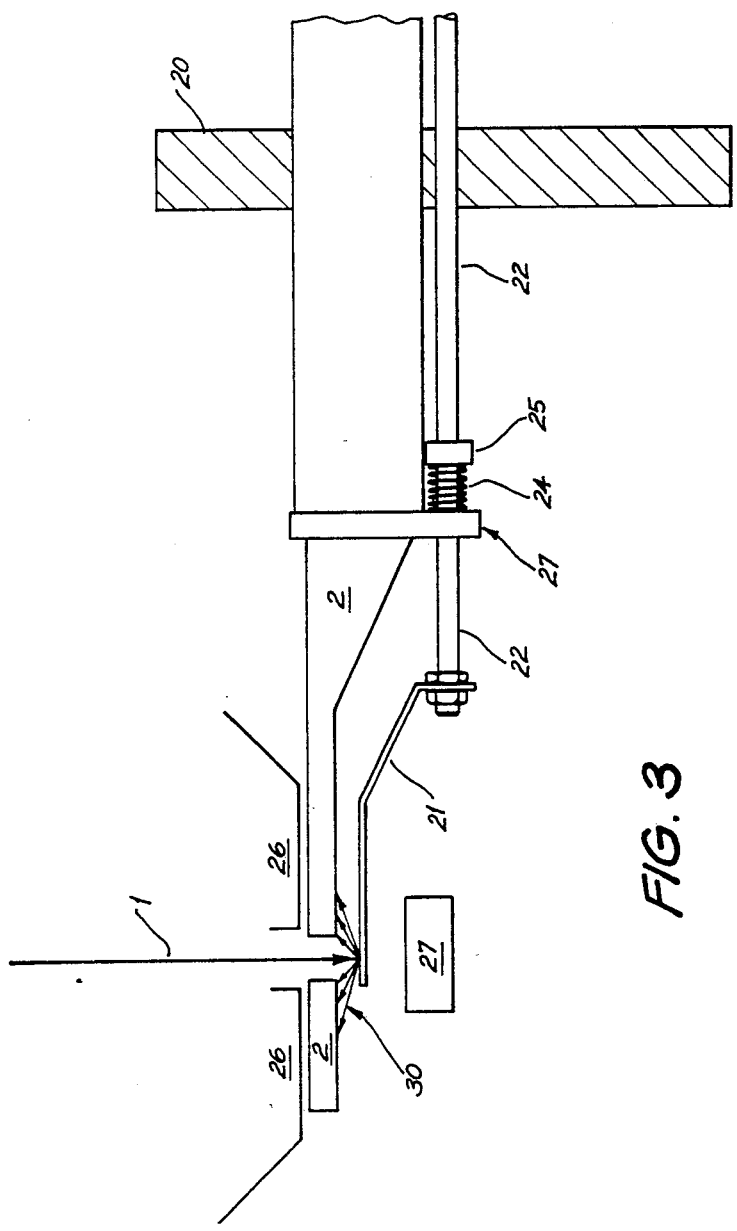
FIG. 3 is a view similar to FIG. 2 but with the calibration device extended into its operative position.

The spring 24 holds the shutter 21 in a rest position as illustrated in FIG. 2 away from the pole piece 26, beam 1, and specimen 27. The rod 22 is able to be pushed against the action of spring 24 to place the shutter 21 in an extended position as illustrated in FIG. 3. In the extended position the detector 2 receives backscattered electrons 30 from the shutter 21 rather than the specimen 27.

Initially the shutter 21 is held away from the beam 1 and the active area of the detector 2. The beam conditions and gain of the detector amplifiers 4, 5 (FIG. 1) are adjusted until a desired detector signal output is achieved. The shutter 21 is then pushed in under the beam 1, which strikes the shutter 21, scattering electrons 30 into the detector 2 and giving off a signal. This signal, which is then noted or recorded, is a direct measure of the electron beam conditions and amplifier settings being employed.

The microscope and analysis systems can then be operated in the normal manner after the shutter 21 has been withdrawn. Generally it is expected that there will be no change to the beam conditions (accelerating voltage, beam current or objective lens settings). Should it be suspected that there has been an alteration in the beam current or amplifier conditions, all that is necessary is that the shutter 21 be again positioned in the path of the electron beam 1. The signal now generated by the detector 2 is compared with the signal previously generated and noted when the shutter 21 was first placed in position. Should the two signals be different, all that is necessary is to readjust the gain of the amplifiers 4, 5 so that the signal currently being generated by the detector 2 is the same as the original signal.

Alternatively, the detector and analysis system can be fitted to a scanning electron microscope or other electron optical equipment fitted with a device for measuring or monitoring the beam current impinging upon the final aperture. Such a device consists of an insulated final aperture and aperture mounting mechanism which is connected to earth potential through a current amplifier or high impedance resistor to a voltage amplifier. The output of this device can then either be monitored and the appropriate compensation made, or it can be fed directly into the digital conversion circuit 8 and logic circuit 9 to compensate for variations of beam current, either by altering the calibration of the system or by automatically readjusting the gain of the amplifier to compensate for the variation of beam current.

The main amplifier 5 can include controls 13 which can take the signal and adjust it to a level which can be fed into the display system, e.g. screen 14, of the electron optical equipment. These controls can include independent D.C. level and signal amplitude controls. They are of a type well known to the industry.

The amplifier 5 feeds the signal into an analogue to digital converter 6, which in turn feeds into a multi-channel analyser 7, the results of which can be accessed by a digital conversion circuit 8 which can incorporate a microprocessor. The microprocessor can communicate with a video display unit 10 and an output unit 11, which may consist of an X-Y recorder, teletype printer, plotter or similar unit. These facilities are all of the type well known in the industry. The logic circuit 9 contains the stored information necessary to convert the signal recorded in the multi-channel analyser into a reading of average atomic number. The principle upon which this is based is outlined in the following section. The digital conversion circuit 8 can set "windows" or data ranges on the multi-channel analyser 7. All counts falling within a particular "window" or range can be fed back into the digital to analogue converter 6, the output of which can be fed into the SEM controls 13. By this method, particular compounds or elements can be visually displayed on the SEM viewing screen 14, either by enhancement of their intensity or by the exclusion of all other phases. By setting more than one "window", it is possible to display two or more phases simultaneously.

PRINCIPLE OF OPERATION

When a high energy electron beam strikes a specimen surface, a number of different signals are generated and a fraction of the incident electrons are scattered back out of the specimen. The number of these electrons scattered out of the surface depends upon the topography, atomic number, crystallographic orientation and internal magnetic and electric fields. Internal electrical fields are eliminated in any specimen which is conducting or has an electrically discharging surface, i.e. is metal or carbon coated or is irradiated in a low vacuum ($\simeq 10$ pa). Crystallographic orientaion effects are integrated and almost completely averaged out when beam convergence exceeds about $10^{-2}$ radian and are destroyed when the specimen is polished. Magnetic field effects apply only to a few specimens, and can be ignored. By eliminating or suppressing the topography component of the backscattered electron signal, this signal is dependent only upon the atomic number factor of the specimen.

Figure 4:
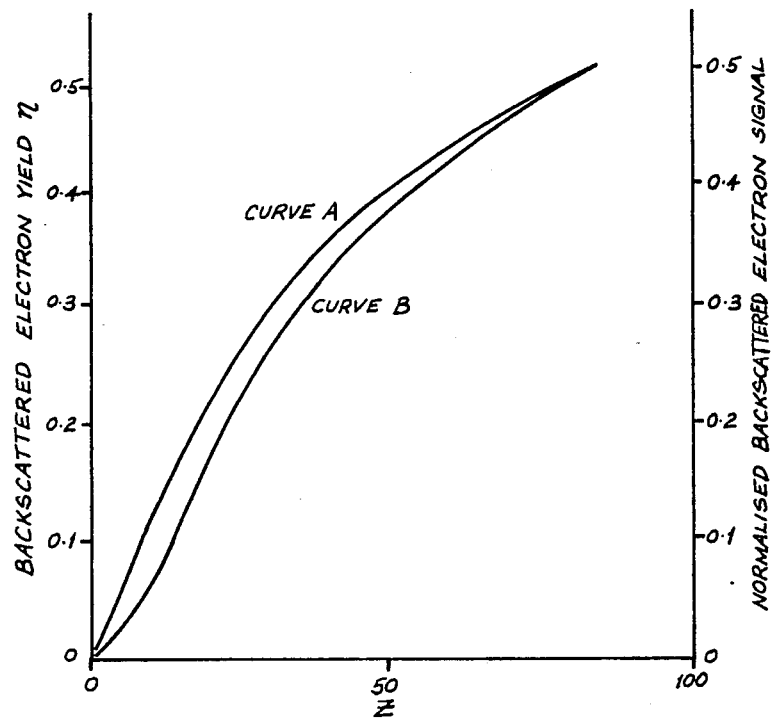
FIG. 4 is a graph of backscattered electron yield and normalised backscattered electron signal as a function of atomic number (Z)
Figure 5:
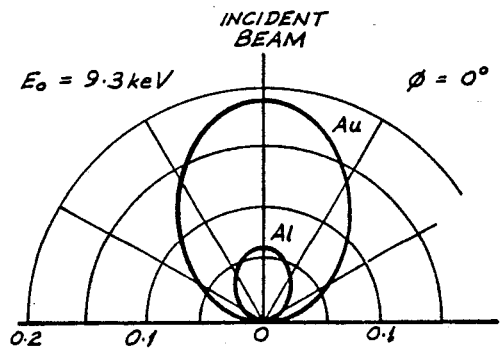
FIG. 5 is a chart illustrating the angular distribution of backscattered electrons.
Figure 6:
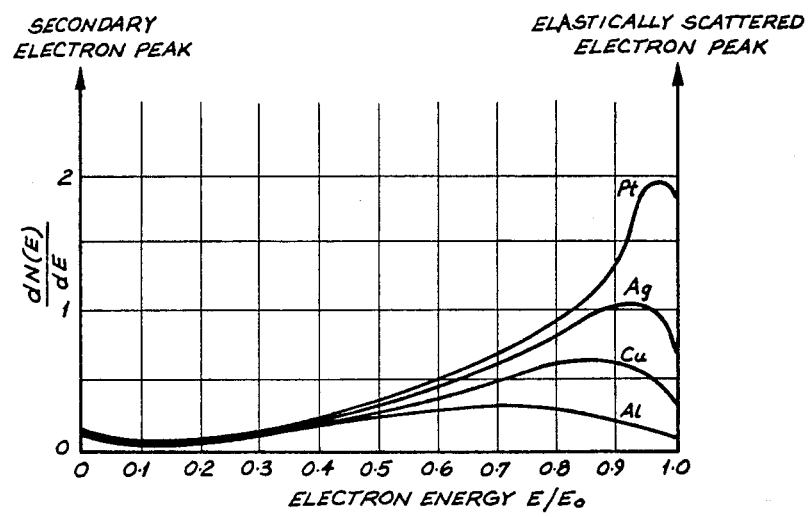
FIG. 6 is a graph illustrating the energy distribution of backscattered electrons.

The variation of backscattered electron yield with atomic number is a monotonically increasing function of atomic number, as shown in FIG. 4, curve A. These electrons emerge at varying angles, being scattered through any angle between $\pi/2$ and $\pi$ radians, see FIG. 5, and can have an energy anywhere between almost zero and the incident beam energy, see FIG. 6. The variation with atomic number of signal output from a backscattered electron detector differs from the backscattered electron yield curve by three major factors, (a) the number and direction of the backscattered electrons detected, (b) the energy of the backscattered electrons, and (c) the detection efficiency of the backscattered electron detector.

The shape of the detector and the distance from the specimen to the detector determines the solid angle subtended by the detectors, which sets the fraction of the backscattered electrons which are detected. The energy of the backscattered electrons is determined by the energy of the incident beam and the atomic number of the sample. The detection efficiency of the backscattered electron detector is determined by the energy of the backscattered electron, the material from which the detector was constructed and the gain of the amplification system.

The variation of backscattered electron detector output with atomic number, is expected to be a different function from the variation of the backscattered electron yield curve with atomic number. This can be expressed $$S_{det} = \eta \cdot \Omega \cdot E_B \cdot I_B \cdot C_E \cdot F(Z) \cdot F(\Omega) \cdot G \qquad (1)$$

where $\eta$ is the backscattered electron yield, $\Omega$ is the solid angle subtended by the detector, $E_B$ is the energy of the primary electron beam, $I_B$ is the incident beam current, Ce is the conversion efficiency of the detector, G is the gain of the amplifiction system and $F(Z)$ and $F(\Omega)$ are functional terms which take into account the variation of backscattered electron energy with atomic number and collection angle respectively. $\Omega$ is fixed by the detector design and working distance. Ce is determined by the material from which the detector is fabricated. $E_B$ and $I_B$ are selected on the microscope. The detector gain G is a detector adjustable parameter.

Figure 7:
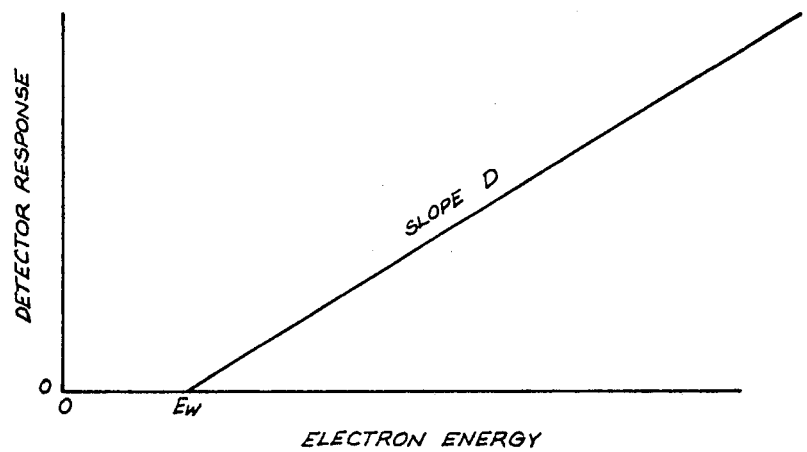
FIG. 7 is a graph of scintillator photomultiplier backscattered electron detector signal output as a function of backscattered electron energy.

Scintillator photomultiplier type backscattered electron detectors show an increase in signal output with electron energy as shown in FIG. 7. The conversion efficiency of the detector is given by:

$$C_e = \frac{D(E_e - E_w)}{E_e} \quad (2)$$

where D is the slope of the line in FIG. 7, $E_e$ is the energy of the electron and $E_w$ is the energy of the surface barrier on the detector. For a material of a particular atomic number, the average energy E of a backscattered electron beam, i.e. $E_3 = F(Z) E_B$, where F(Z) is dependent upon Z and varies between 0.5 for low Z to 0.9 for high Z. Substituting equation (2) into equation (1) gives:

$$S_{det} = \eta \cdot \Omega[E_B - [(E_W)/F(Z)]]I_B \cdot F(Z) \cdot F(\Omega) \cdot G \quad (3)$$

From equation (3), we can see that for a given sample, fixed Z and $\eta$, in a particular SEM, the same detector output can be achieved despite variations in operating parameters, simply by adjusting the detector gain G, according to the following relationships:

($I_B \cdot G$) = constant
[$E_B - (E_w/F(Z))$]G = constant, provided F(Z) remains constant, which it does at accelerating voltages above 15 keV (Colby 1969).
$\Omega F(\Omega)G$ = constant, provided $F(\Omega)$ remains constant, which it should be expected to do for small variations in $\Omega$.

When the beam current, accelerating voltage, detector geometry and gain are fixed, the detector signal varies with atomic number according to the relationship $$S_{det} \alpha \ \eta F(Z) \ (\Omega)$$

$\alpha \ \eta F(Z)$, since $\Omega$ is constant.

Thus, the signal output from any backscattered electron detector can be expected to be given by:

$$S_{det} = K \ \eta F(Z) \quad (4)$$

where K is a constant and is dependent upon $E_B$, $I_B$, $\Omega$, $E_w$, D and G. $E_w$ and D are determined by the detector and for optimum performance $E_w$ should be as low as possible and D as high as possible. $\Omega$ is determined by specimen working distance. $E_B$ and $I_B$ are instrument parameters. However, it should be expected that any variation in these five parameters can always be exactly compensated for by a variation in the detector amplification such that the same shape curve always applies (at least for $E_B$ greater than 10 kV and small variations in $\Omega$). Very little work has been done on the variation of $F(\Omega)$. Results suggest that $F(\Omega)$ increases with specimen tilt and low take off angles, but that for a high take off angle detector, $F(\Omega)$ is constant over a wide range of $\Omega$, even for specimen tilts over a range of $\pm 10°$.

It should be noted that although the constant K in equation 4 is dependent upon $E_B$, $I_B$, $\Omega$, $E_w$, D and G, any variation in the first 5 parameters can be exactly compensated for by the appropriate change in the detector amplification setting. That is, the curve of detector signal versus atomic number is independent of the detector, beam voltage and working distance employed (within the constraints mentioned above).

Figure 8:
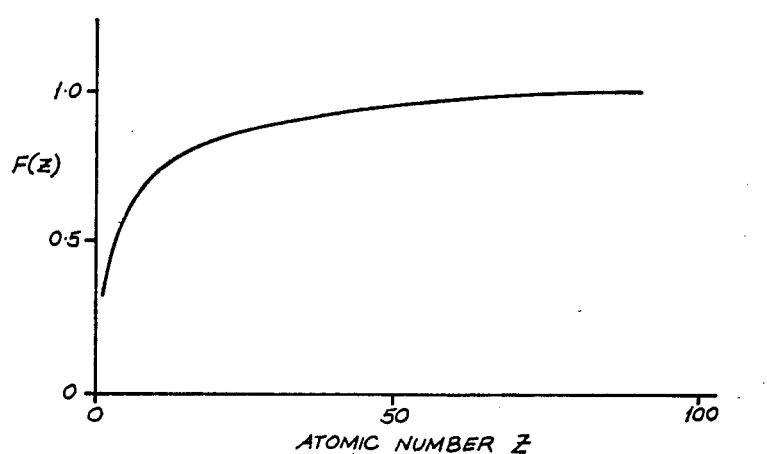
FIG. 8 is a graph of F(Z) normalised for bismuth.

The variation of the calibration electron detector signal with atomic number can be measured, and is shown, curve B in FIG. 4, normalised with the backscattered electron yield curve for bismuth, atomic number 83. Like the backscattered electron yield curve, the backscattered electron detector output signal curve is also a monotonically increasing function of atomic number. The difference between the two curves is F(Z). F(Z) is shown in FIG. 8, normalised at $F(Z)_{82} = 1.0$.

By normalising the detector output at any two points on the curve, the detector/microscope system can then be calibrated with curve B, FIG. 4. By noting the signal from any sample of unknown composition, the atomic number factor of the sample can be simply extrapolated from the curve, see FIG. 9. When the sample is a pure element having unit atomic number, identification is exact, providing experimental error is not too large. Determination of the atomic number factor from a compound or number of elements is a little more complex. The signal that would be obtained from a combination of elements can be determined from the relationship S:

$$S_{comp} = \sum_{i=1}^{n} X_i S_i \quad (5)$$

where $S_{comp}$ is the backscattered electron signal from the compound, $X_i$ is the weight fraction of the $i^{th}$ element, and $S_{fi}$ is the backscattered electron signal of the $i^{th}$ element in the compound. $X_i$ is given by:

$$X_i = \frac{A_i}{\sum_{j=1}^{n} N_j A_j} \quad (6)$$

where $A_i$ and $A_j$ are atomic weights and $N_j$ is the number of atoms of component j in one molecule of the compound.

Figure 9:
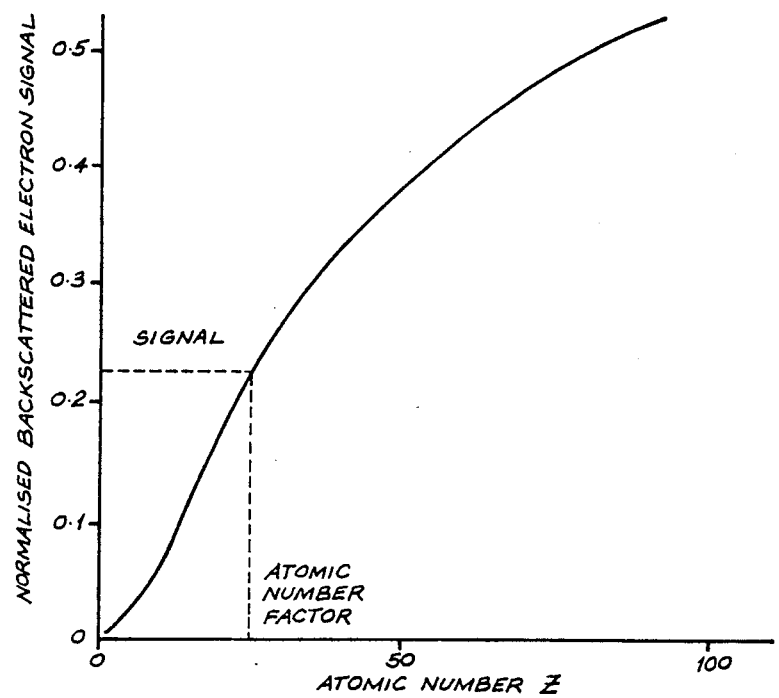
FIG. 9 is a graph of normalised backscattered electron signal as a function of atomic number.

The atomic number factor (ANF) is then determined by extrapolating from the signal versus atomic number curve, again as is shown in FIG. 9.

Note that Castaing in 1960 (R. Castaing, Electron Probe Microanalysis, Adv. Electron. Electron Phys, Ed. L. L. Martin and C. Marton, Academic Press, New York, 13 (1960) 317–386), developed a similar relationship to that in equation 5. His expression was:

$$\eta_{comp} = \sum_{i=1}^{n} X_i \eta_i$$

where $\eta_{comp}$ and $\eta_i$ were the backscattered electron yields of the compound and the $i^{th}$ element of the compound respectively. As pointed out in equations 1 and 3 above there is a complex relationship between the backscattered electron yield $\eta$ and the backscattered electron detector signal output S. As such it is not al all obvious that equation 5 follows directly from the Castaing relationship. For example, in 1969, Colby (J. W. Colby Backscattered and secondary electron emission as ancillary techniques in electron probe analysis in Adv. Electron. Electron Phys. Suppl. 6, Ed. A. J. Tousimis and L. Martin, Academic Press, New York, 177–196 (1969)) again used only the Castaing relationship given above, not the relationship used in equation 5.

Equation (5) assumes an amorphous or polycrystalline structure containing no voids or imperfections other than those normally associated with grain boundaries and lattice defects. These imperfections are generally of the order of atomic dimensions and are usually uniformly distributed throughout the electron beam interaction volume. As such, they produce no variations in detector signal. Larger voids and imperfections will produce a reduction in detector signal output below that computed in equation (5). This can be compensated for by the addition of a variable multiplying factor F in equation 5, such that:

$$S_{comp} = F \sum_{i=1}^{n} X_i S_i \qquad (7)$$

F can be any number between 0 and 1.0. It can be included as an optional extra in the logic unit used to control the microprocessor. F can be set at less than 1.0, or calculated to be less than 1.0, enabling the extent of imperfections to be accounted or calculated. To a first approximation, F is dependent upon specimen density and is given by $$F = \rho 40 / \rho \qquad (8)$$

where $\rho'$ is actual density of the sample and $\rho$ is the theoretical density of a sample free from voids and imperfections.

The foregoing describes a system which enables determination of a unit herein termed the atomic number factor, when a sample is examined in a scanning electron microscope fitted with one of these systems, and it has also been shown how this atomic number factor is related to the chemical composition of the sample being analysed. However, that relationship only enables verification of a known composition. It does not enable the composition of an unknown material to be predicted.

The relationships in equations 5 and 6, when considered with valence possibilities, do enable possible compositions to be calculated. Valence considerations can be expressed as $$\sum_{i=1}^{n} N_i \cdot V_i = 0 \qquad (9)$$

where $N_i$ and $V_i$ are respectively the number and valence state of the $i^{th}$ ion, and n is the number of ions in the compound.

Equation 9 can be combined with equations 5 and 6 such as to yield a set of three simultaneous equations.

Energy dispersive X-ray spectroscopy can yield data relating to the relative concentrations of the heavy elements, for atomic number 9 and greater. These results, when combined with the three equations 5, 6 and 9, can be used to quantify the composition of the material being examined.

The preferred mode of operation of the analysis system is set out below.

The scanning electron microscope is turned on and used to image a material of known composition. The gain of the detector is adjusted such that a convenient detector signal output is measured when the standard is being imaged. The digital conversion and processing unit is informed that this signal corresponds to the atomic number factor of the known material. This is repeated for another known material. The digital processing unit then adjusts the read out of the detector signal to read directly in terms of atomic number factor.

A record is made of the beam current conditions currently employed. This can be either a read out of the beam current at the final aperture, or the shutter can be inserted and the detector signal output voltage recorded.

The standards are then moved out of the field of view and the sample to be examined is moved into the field of view. The signal from the detector is displayed on the multi-channel analyser and the channels into which the signals fall are calibrated directly in the atomic number factor.

If at any stage that it is suspected that the beam current may have drifted, all that is necessry is to reinsert the shutter, and compare the current detectorvoltage with the earlier recorded voltage. if the voltages are different, either adjust the gain of the detector until the voltage is the same or feed the two voltages into the digital processing unit and it will readjust the calibration scale. Alternatively, by monitoring the beam current at the final aperture, the calibration scale can be readjusted by feeding the beam current variation into the digital processing unit.

The foregoing describes only some embodiments of the present invention and modifications, obvious to those skilled in the art, can be made thereto without departing from the scope of the present invention.

What we claim is:

1. An analysis sytem for determining the atomic number factor of a region of a specimen, system being adapted for connection to a scanning electron microscope or equivalent device for generating and controlling an electron beam which impinges on the region of the specimen, said system comprising a backscattered electron detector having an output indicative of the average energy of all electrons backscattered by said region, an amplifier connected to the output of said detector, a processing circuit to receive the output of said amplifier, an analog to digital converter connected to the output of said amplifier, a multi-channel analyser connected to the output of said digital to analog converter, and said processing circuit comprises a digital conversion and processing circuit connected to the output of said multi-channel analyser, the output of the processing circuit being in accordance with the relationship $$S = K \cdot \eta \cdot F(Z)$$

where
S is the amplified output of the backscattered electron detector,
K is a constant determined by the operational conditions of the scanning electron microscope or equivalent device,
$\eta$ is the fraction of electrons backscattered by said region, and
F(Z) is the difference between the backscattered electron yield curve for materials of known atomic number factor and the amplified backscattered electron detector output signal curve for the same materials of known atomic number factor, to thereby indicate the atomic number factor of said region, and means to display and/or record the output of said processing circuit.

2. An analysis system as claimed in claim 1 wherein said region comprises a compound formed from a plurality of elements or a mixture of a plurality of elements, wherein said specimen has been subjected to energy dispersive x-ray spectroscopy and the output of the energy dispersive x-ray detector system including data of the relative intensity of detected ones of said plurality of elements able to be so detected and the identity of possible ones of said elements not able to be so detected, is connected to said digital conversion and processing circuit which calculates an expected electron backscattered detector output signal for each detected or possible element, multiplies each expected output signal with a weight fraction corresponding to that element, the weight fraction being determined by an estimated chemical formula, sums the products thereby obtained to arrive at an expected backscattered detector signal for the region, and converts the expected backscattered electron signal to an expected atomic number factor which is displayed for comparison with the atomic number factor of the region.

3. An analysis system as claimed in claim 2 wherein the digital conversion and processing circuit includes data of possible valence combinations of said detected and possible elements and calculates the chemical formula for the determination of said weight fraction.

4. An analysis system as claimed in claim 1 including monitor means to monitor the beam current of said detector beam.

5. An analysis sytem as claimed in claim 4 wherein said monitor means comprises a beam current monitoring device attached to the final aperture of said scanning electron microscope or equivalent device and wherein the output of said beam current monitoring device is used in a feedback loop to control the output of said analysis system.

6. An analysis system as claimed in claim 5 wherein the output of said beam current monitoring device is applied to said amplifier connected to said detector to control the gain of said amplifier.

7. An analysis system as claimed in claim 5 wherein the output of said beam current monitoring device is applied to said digital conversion and processing circuit to effectively re-calibrate said display means.

8. An analysis system as claimed in claim 4 wherein said monitor means comprises an electron scattering or deflecting member externally movable relative to said detector to locate said scattering or deflecting member in, or affect the path of, said electron beam to scatter or deflect part or all of said beam into at least a portion of the active detection region of said detector or place at least a portion of the active region of said detector directly in the path of said electron beam.

9. An analysis system as claimed in claim 8 wherein said electron scattering or deflecting member comprises a metal shutter movable relative to said detector and resiliently biassed out the path of said electron beam.

10. An analysis system as claimed in claim 9 wherein said shutter comprises a plate mounted on a rod, a helical spring is located on said rod to urge said plate out of the path of said electron beam, and said rod is movable to compress said spring and move said plate into said path whereby backscattered electrons from said plate are received by said backscattered electron detector.

* * * * *